United States Patent [19]

Lewis

[11] Patent Number: 4,692,698

[45] Date of Patent: Sep. 8, 1987

[54] METHOD AND DEVICE INCLUDING A BED OF FERROMAGNETIC FIBERS AND MAGNETIC FLUX SENSOR FOR MEASURING THE AMOUNT OF MAGNETIC PARTICLES ON A LIQUID

[75] Inventor: Robert T. Lewis, Albany, Calif.

[73] Assignee: Tribometrics, Inc., Berkeley, Calif.

[21] Appl. No.: 860,575

[22] Filed: May 7, 1986

Related U.S. Application Data

[63] Continuation-in-part of Ser. No. 764,552, Aug. 12, 1985.

[51] Int. Cl.$^4$ .................... G01N 27/74; G01R 33/12
[52] U.S. Cl. .................... 324/204; 324/71.1; 324/235; 340/631
[58] Field of Search .................... 324/204, 235, 71.1, 324/71.4; 73/53, 61 R; 340/627, 631

[56] References Cited

U.S. PATENT DOCUMENTS 4,492,921 1/1985 Sandulyak et al. ............ 324/204

FOREIGN PATENT DOCUMENTS 59-54956 3/1984 Japan.
0702304 12/1979 U.S.S.R. .................... 324/204

Primary Examiner—Gerard R. Strecker

[57] ABSTRACT

An improved method and device for measuring magnetic particles in a liquid wherein a known amount of liquid is contacted with a bed of ferromagnetic fibers maintained in the magnetic field of a magnet with sufficient strength to substantially completely magnetize said particles for a time long enough for said particles to migrate to and be substantially completely captured by said fibers and having a magnetic flux sensor positioned between a pole face of said magnet and said bed wherein the distance from said sensor to the fibers farthest from said sensor is not greater than about 6 millimeters.

16 Claims, 3 Drawing Figures

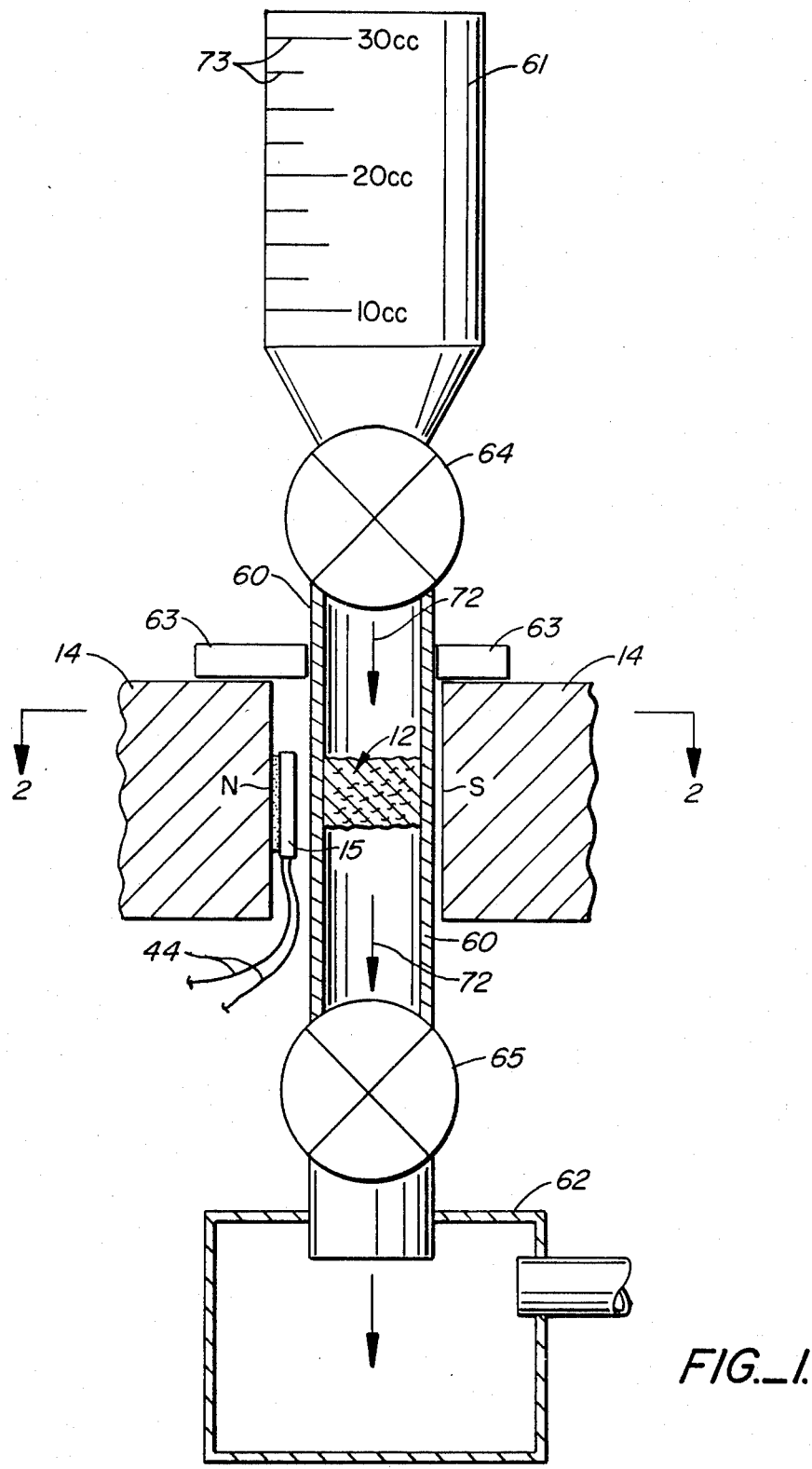
FIG._1.

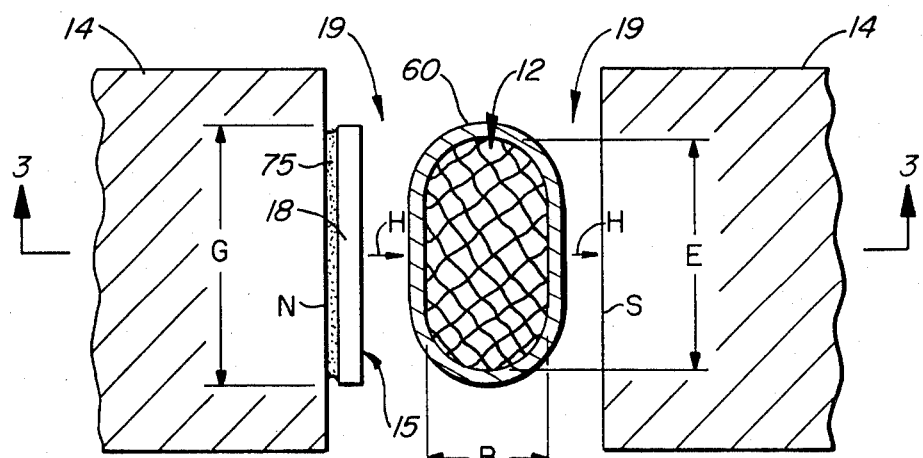
FIG._2.
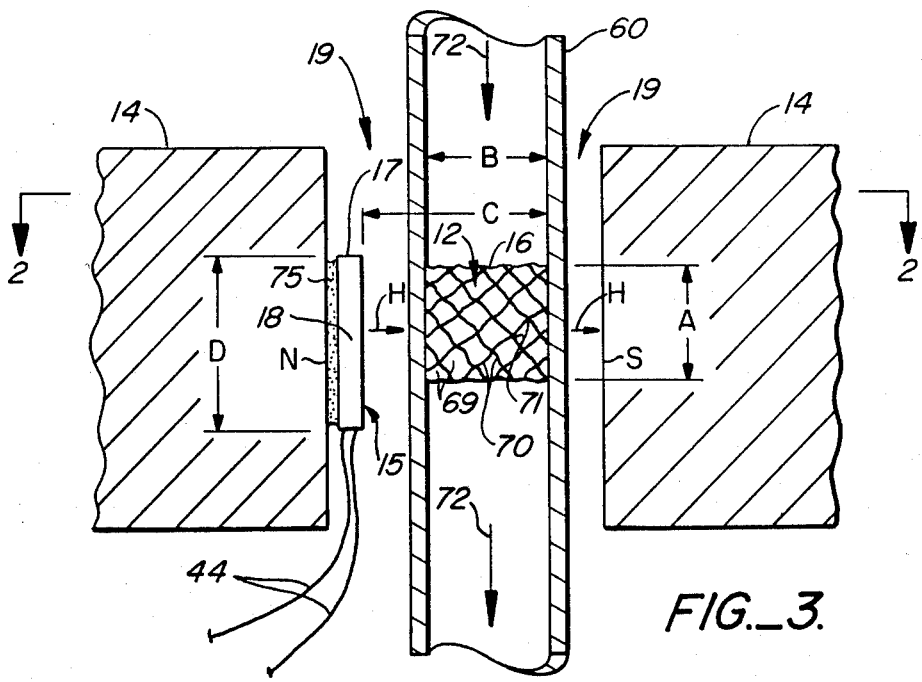
FIG._3.

METHOD AND DEVICE INCLUDING A BED OF FERROMAGNETIC FIBERS AND MAGNETIC FLUX SENSOR FOR MEASURING THE AMOUNT OF MAGNETIC PARTICLES ON A LIQUID

This application is a continuation in part of application Ser. No. 06/764,552 filed 08/12/85 entitled "METHOD AND DEVICE FOR MEASURING MAGNETIC PARTICLES IN A FLUID."

BACKGROUND OF THE INVENTION

It is well known that lubricants such as oil are commonly used to minimize wear in operating machine parts such as transmissions, gearboxes, hydraulic systems and engines used in aircraft, helicopters, ships, locomotives, trucks, automobiles, stationary engines and pumps as examples. However, in spite of lubrication, particles wear from rubbing and bearing surfaces and deposit in the lubricant. It has long been recognized that knowledge about the amount and form of these wear particles can give valuable information concerning the condition of the machine. In particular, it has been recognized that the presence of metallic wear particles is an indication of the presence of an abnormal wear condition. In many cases metallic particles larger than 10 microns are produced by said abnormal wear condition. When said abnormal wear condition is starting said particles are present in very small amounts, even less than 10 micrograms per cubic centimeter. Therefore sensitive techniques for detecting said particles are needed in order to give early warning of said abnormal wear condition.

Since the highly stressed rubbing and bearing surfaces in modern machines are usually made of cast iron or steel the wear particles from these surfaces contain iron.

Many techniques have been used to analyze for iron containing wear particles in used lubricants. One current method is to periodically sample the lubricant and submit it for laboratory analysis by spectroscopy. However, spectroscopy does not distinguish metallic iron and steel from other forms of iron such as oxides and corrosion products not associated with said abnormal wear condition. In addition, it is insensitive to particles larger than about 8 microns. Furthermore, it requires an expensive laboratory instrument and is, consequently, not available to many machine operators.

Since metallic iron and steel are strongly magnetic, special magnetic techniques have been used to detect metallic iron and steel wear particles. In one such technique the particles are magnetically deposited on a glass slide. After suitable washing and fixing, the amount deposited is determined from the optical density of the deposit. However, other materials, less magnetic than metallic iron and steel, such as carbonaceous combustion products, basic sulfates, oxides, corrosion products and the like, also deposit and contribute to the optical density. Consequently optical density is a poor measure of the amount of metallic iron and steel wear particles.

Some machines contain magnetic chip detectors in their lubricant reservoirs that collect iron and steel wear particles from the passing circulating lubricant. However, these detectors are insensitive to particles smaller than about 100 microns and do not provide a quantitative measure of the amount of metallic iron and steel wear particles in the lubricant. They are, of course, only useful for machines in which they are already installed.

A method for measuring the quantity of magnetic particles in a fluid has been described in Japanese Patent Application Kokai No. 59-54956(54956/1984). This method is characterized by a magnetic collecting part to collect the magnetic particles and a magnetic flux sensor to measure the quantity collected. However, the method as described, while quite suitable for measuring the performance of electromagnetic filters, does not have sufficient sensitivity and accuracy for measuring the amount of iron and steel wear particles in a sample of lubricant from a machine for the purpose of giving early warning of an abnormal wear condition.

SUMMARY OF THE INVENTION

It is an object of this invention to provide a sensitive, and accurate method and device for measuring the amount of magnetic particles in a liquid such as metallic iron and steel wear particles in a sample of lubricant from a machine.

It is a further object of this invention to provide improvements to the method described in Japanese Patent Application Kokai No. 59-54956(54956/1984) for its use in measuring magnetic particles in a sample of liquid such as metallic iron and steel wear particles in a sample of lubricant from a machine.

These and other objects are achieved with a bed of ferromagnetic fibers maintained in the field of a magnet with sufficient strength to substantially completely magnetize said magnetic particles. A field of at least 1500 Oersted is preferred for iron and steel wear particles for example. A magnetic flux sensor is positioned between a pole face of said magnet and said bed wherein the distance from said sensor to the fibers in said bed farthest from said sensor is not greater than about 6 millimeters. Said sensor includes known means to record the magnitude of the flux sensed. The magnetic flux from said bed is measured to obtain a first flux value. An amount of said liquid is measured and said measured amount of liquid is caused to flow through said bed at a flow rate sufficiently slow to provide a contact time between said liquid and said bed for said magnetic particles to migrate to and be substantially completely captured by said fibers. A contact time of at least 0.1 seconds is preferred for iron and steel wear particles for example. Said liquid may be mixed with a suitable solvent before contacting said bed to reduce the viscosity of said liquid and thereby enhance migration of said particles to said fibers. A viscosity of less than about 2 centipoise is preferred for iron and steel wear particles for example. The magnetic flux from said bed with said captured particles is measured with said sensor to obtain a second flux value. Said first flux value is subtracted from said second flux value to obtain a difference that is representative of the amount of magnetic particles in said measured amount of liquid. Said sensor is calibrated by removing said bed, measuring the flux to obtain a first flux value, inserting a known amount of magnetic particles in place of said bed, measuring the flux to obtain a second flux value, subtracting said first flux value from said second flux value whereby a difference is obtained that is representative of a known amount of magnetic particles.

BRIEF DESCRIPTION OF THE DRAWINGS

FIG. 1 is a flow diagram of a plan view of the device of this invention.

FIG. 2 shows a section in the plane 2—2 of FIG. 1 perpendicular to the direction of liquid flow.

FIG. 3 shows a section in the plane 3—3 in FIG. 2 parallel to the directions of liquid flow and magnetic field.

DETAILED DESCRIPTION OF THE INVENTION

The direction of liquid flow is shown by the arrows in FIGS. 1 and 3 and where the liquid enters will be called the top of the bed and where the liquid exits will be called the bottom of the bed.

It has been found that considerable enhancement of the detection of the magnetic flux by a flux sensor, and consequently considerable improvement in the sensitivity of a device using the method for measuring magnetic particles in a fluid described, for example, in Japanese Patent Application Kokai No. 59-54956(54956/1984) can be achieved with certain geometrical arrangements between a bed of fibers, said flux sensor and the pole faces of a magnet.

One such arrangement is illustrated in FIGS. 1, 2 and 3. A bed of fibers 12 in a tube 60 is positioned in a liquid flow path 72 between the north and south pole faces, designated N and S respectively, of a magnet 14 with a magnetic field H between said pole faces. The vertical dimension A of bed 12 is preferably about 2 millimeters. Bed 12 has a dimension B perpendicular to the direction of flow path 72 such that the distance C from sensor 15 and the fibers in bed 12 farthest from sensor 15 is not greater than about 6 millimeters. The direction of magnetic field H is perpendicular to the axis of flow path 72. A flux sensor 15 is positioned between bed 12 and one of the pole faces of magnet 14 say the north pole face N as example. The vertical dimension D of sensor 15 is preferably greater than the vertical dimension A of bed 12 but less than about twice the vertical dimension A of bed 12. Sensor 15 is equiped with wires 44 to transmit the strength of the flux sensed to knwon equipment, not shown, to record the magnitude of the flux sensed. Bed 12 may have a circular cross-section perpendicular to the axis of flow path 72. The dimension B of said circular cross-section is preferably about 2 millimeters and in no case greater than about 6 millimeters.

Bed 12 may have an oblong cross-section perpendicular to the axis of flow path 72 with the short axis of said oblong cross-section extending between the pole faces of magnet 14. Said oblong cross-section results in the capture of more particles near sensor 15 and thereby further enhances sensitivity. Dimension B of said oblong cross-section is preferably about 2 millimeters and in no case greater than about 6 millimeters. Dimension G of sensor 15 is preferably about equal to dimension E of said oblong cross-section but less than about twice said dimension E. The thickness of sensor 15 in the direction parallel to the magnetic field H is preferably less than about 1 millimeter.

It has been found that particles are preferentially captured at the top surface 16 of bed 12. Consequently, surface 16 is preferably below the top 17 of sensor 15 but above the center 18 of sensor 15. Sensor 15 is preferably bonded to the pole face of magnet 14 with cement 75. Cyanoacrylic cement has been found to be a suitable cement. Tube 60 is preferably surrounded by a space 19 filled with thermally insulating material such as plastic. Space 19 is preferably about 0.2 millimeters wide in the direction parallel to the magnetic field H. Bed 12 can be made from any suitable ferromagnetic material. Low carbon and ferritic steel wool with openings 69 between fibers 70 are two suitable materials for example. Said wool preferably has fibers 70 with diameters about two times the average major dimension of the smallest particles to be captured. The long axes of said fibers 70 are preferably substantially perpendicular to magnetic field H. Bed 12 can be formed, for example, by compressing said wool into tube 60 with a pressure generally in the range of about 20 kilograms per square centimeter to about 300 kilograms per square centimeter. Said pressure can be used to vary the size of openings 69 between fibers 70. Larger openings 69 are desired to pass non-magnetic particles that would block smaller openings 69. Smaller openings 69 result in more rapid capture of magnetic particles. It has generally been found desirable to restrict the movement of fibers 70 during liquid flow by cementing fibers 70 with cement 71. Cement 71 should be insoluble in the liquid and not tacky to the particles if subsequent removal of the particles is desired. One such cement, suitable for use with lubricating oils, is a mixture of Duco cement in acetone. Duco cement is the Trademark of a butyl acetate cement available commercially. The amount of cement 71 used should be enough to cement fibers 70 but not block openings 69. The inside cross-section of tube 60 is chosen to correspond to the cross-section of bed 12. The wall thickness of tube 60 is preferably less than about 0.3 mm. Tube 60 is preferably made of any suitable non-magnetic material such as brass, aluminum or plastic.

A buret 61 with graduations 73 is attached to the top of tube 60 with an inlet valve 64. Tube 60 is held in place with a clamp 63. Clamp 63 is made of any suitable non-magnetic material such as brass, aluminum or plastic. A receiving vessel 62 is provided to receive liquid that has flowed through the device. Receiving vessel 62 is attached to the bottom of tube 60 with an outlet valve 65 to control flow.

A sample of liquid to be measured is poured into buret 61 with inlet valve 64 closed. A measured amount of said sample is obtained using graduations 73. The magnetic flux is measured with sensor 15 to obtain a first flux value. Inlet valve 64 is opened and said sample is caused to flow along flow path 72 through tube 60, bed 12 and into receiving vessel 62 by means, not shown, using pressure, vacuum or gravity. The flow rate of said sample through bed 12 is controlled with outlet valve 65 to give a contact time of at least about 0.1 sec between said sample and bed 12. After the entire measured sample has contacted bed 12 the flux is measured with sensor 15 to obtain a second flux value. Said first flux value is subtracted from said second flux value to obtain a difference that is representative of the amount of magnetic particles in said sample. Said amount of magnetic particles is divided by said measured amount of sample to obtain the amount of magnetic particles in said liquid.

EXAMPLE I

A sample of used lubricating oil from the crankcase of the engine of a 1967 JEEP Wagoneer, obtained shortly after engine operation, that was experiencing an abnormal valve train wear condition was mixed with an equal amount of petroleum solvent. Said mixture was found to have a viscosity of 1.97 centipoise with an Ostwald viscometer. 28 cubic centimeters of said mixture was poured into buret 61 to obtain a measured amount of mixture. Tube 60 was made of brass and had a circular cross-section with an inside diameter of 2.5 millimeters and a wall thickness of 0.3 millimeters. Tube 60 contained a bed of fibers 12 made by compressing 14 milligrams of grade 0000 low carbon steel wool with 5 drops of a mixture of 15% Duco cement in acetone with a pressure of 180 kilograms per square centimeter and allowed to dry 16 hours. Grade 0000 steel wool has fibers 15 microns in diameter. Bed 12 was positioned between the pole faces of a permanent magnet 14 with distance between the pole faces of 4.8 millimeters and a magnetic field strength H between the pole faces of 1600. Oe. Said field is known to be 100. Oe greater than the field known to be required to substantially completely magnetize metallic iron and steel wear particles. A flux sensor 15 of the Hall generator type with dimension D equal to 2 millimeters and the dimension G equal to 1 millimeter and having a thickness equal to 0.5 millimeters was positioned between the north pole face of magnet 14 and tube 60 with bed 12 so that the top of bed 12 was 0.5 millimeters below the top 17 of sensor 15. The magnetic flux was measured with sensor 15 to obtain a first flux value. Said measured amount of mixture was drawn through bed 12 with a vacuum pump, not shown, at a rate that gave a contact time in bed 12 greater than 0.1 sec. During flow of said measured amount through bed 12 metallic iron and steel wear particles larger than about 5 microns migrated to and were substantially captured by fibers 70. After the entire measured amount had contacted bed 12 the magnetic flux was measured with sensor 15 to obtain a second flux value. Said first flux value was subtracted form said second flux value to obtain a difference that corresponded to 280 micrograms of metallic iron. Said measured amount of magnetic particles was divided by said measured amount of used lubricating oil equal to 14 cubic centimeters to give the amount of magnetic particles in said used lubricating oil equal to 20 micrograms of metallic iron per cubic centimeter.

EXAMPLE II

A sample of used oil was obtained from the same source as in example I but 1828 miles after repair of said valve train including an oil and filter change. Said sample was processed in the same manner as the sample in example I. The amount of magnetic particles in said sample was measured to be less than 0.1 micrograms of metallic iron per cubic centimeter.

What is claimed is:

1. A device for measuring the amount of magnetic particles in a liquid, said device including a magnet, a bed of ferromagnetic fibers supported in the magnetic field of said magnet to capture said particles as said liquid is passed through said bed and a means to measure the magnetic flux of the captured particles, wherein the improvement comprises:

means providing a flow path for said liquid including said bed and a means to flow a known amount of said liquid along said flow path through said bed, said magnet comprising a pair of pole faces between which said bed is supported and having sufficient strength to substantially completely magnetize said particles, and said means to measure the magnetic flux comprising a magnetic flux sensor positioned between a pole face of said magnet and said bed, said bed being dimensioned such that the distance from said sensor to the fibers in said bed farthest from said sensor is not greater than about 6 millimeters.

2. The device of claim 1 wherein said magnet is a permanent magnet with a field strength of at least fifteen hundred Oersted.

3. The device of claim 1 wherein the distance between said flux sensor and said bed is less than about 1 millimeter and said flux sensor is cemented to said pole face.

4. The device of claim 1 wherein the extent of said flux sensor in a direction axial to said flow path is greater than the extent of said bed axial to said flow path and less than about twice the extent of said bed axial to said flow path.

5. The device of claim 1 wherein said bed has an oblong cross-section perpendicular to the axis of said flow path with the short axis of said oblong cross-section extending between the pole faces of said magnet.

6. The device of claim 1 wherein the inlet of said bed is located below the top and above the center of said flux sensor.

7. The device of claim 1 wherein the diameter of said fibers is about two times the average major dimension of the smallest particles to be captured.

8. The device of claim 1 wherein the fibers in said bed are compressed with a pressure of from about twenty to about three hundred kilograms per square centimeter.

9. The device of claim 1 wherein said fibers are cemented in place.

10. The device of claim 1 wherein the long axes of said fibers are substantially perpendicular to said magnetic field.

11. The device of claim 1 including thermal insulation between said bed and said flux sensor.

12. The device of claim 1 wherein said flux sensor is a Hall type generator that is less than about five millimeters in a direction parallel to the axis of said flow path, less than about ten millimeters in a direction perpendicular to the axis of said flow path and said magnetic field and less than 1 millimeter thick in a direction parallel to said magnetic field.

13. A method for measuring the amount of magnetic particles in a liquid comprising: maintaining a bed of ferromagnetic fibers in the magnetic field between the pole faces of a magnet strong enough to substantially completely magnetize said particles to be measured, positioning a means to measure the magnetic flux from said bed between a pole face of said magnet and said bed wherein the distance between said means and the fibers farthest from said means is not greater than about 6 millimeters, measuring the magnetic flux from said bed to obtain a first flux value, passing a measured amount of said liquid through said bed at a flow rate sufficiently slow to permit said magnetic particles to become substantially completely captured by the fibers in said bed, measuring the flux value from said bed to obtain a second flux value, subtracting said first flux value from said second flux value to obtain a difference that is representative of the amount of magnetic particles in said 14. The method of claim 13 whereby said difference is calibrated by removing said bed, measuring the flux to obtain a first flux value, inserting a known amount of magnetic particles in place of said bed, measuring the flux to obtain a second flux value, subtracting said first flux value from said second flux value to obtain a difference that is representative of a known amount of magnetic particles.

15. The method of claim 13 wherein said flow rate is sufficiently slow to provide a contact time between said liquid and said bed of at least 0.1 seconds.

16. The method of claim 13 wherein said liquid is mixed with a solvent before contacting said bed.

* * * * *

UNITED STATES PATENT AND TRADEMARK OFFICE
CERTIFICATE OF CORRECTION

PATENT NO. : 4,692,698

DATED : September 8, 1987

INVENTOR(S) : Robert T. Lewis

It is certified that error appears in the above-identified patent and that said Letters Patent is hereby corrected as shown below:

Column 6, line 54, "in said" should read -- in said liquid --.

Signed and Sealed this

Sixteenth Day of February, 1988

Attest:

DONALD J. QUIGG

Attesting Officer

Commissioner of Patents and Trademarks